United States Patent [19]

Lewis

[11] Patent Number: 5,364,415
[45] Date of Patent: Nov. 15, 1994

[54] OXIDATIVE HAIR DYE COMPOSITIONS AND PROCESSES UTILIZING LEUCO VAT DYES

[75] Inventor: David M. Lewis, Otley, United Kingdom

[73] Assignee: Clairol Inc, New York, N.Y.

[21] Appl. No.: 67,894

[22] Filed: May 27, 1993

[51] Int. Cl.$^5$ ............................ A61K 7/13; C09B 9/00
[52] U.S. Cl. .................................. 8/406; 8/405; 8/407; 8/408; 8/642; 8/650; 8/651
[58] Field of Search .................. 8/405, 406, 407, 408, 8/642, 650, 651

[56] References Cited

U.S. PATENT DOCUMENTS

| | | | |
|---|---|---|---|
| 2,721,211 | 10/1955 | Buc | 8/651 |
| 2,906,587 | 9/1959 | Lantz et al. | 8/32 |
| 3,607,488 | 10/1971 | Yordán | 156/57 |
| 3,918,896 | 11/1975 | Kalopissis et al. | 8/10.2 |
| 4,605,419 | 8/1986 | Kikuchi et al. | 8/405 |

Primary Examiner—Paul Lieberman
Assistant Examiner—Caroline L. Dusheck
Attorney, Agent, or Firm—Morton S. Simon

[57] ABSTRACT

Leuco vat dyes are employed to produce brighter shades from oxidative dyes in oxidative haircoloring systems and processes.

11 Claims, No Drawings

OXIDATIVE HAIR DYE COMPOSITIONS AND PROCESSES UTILIZING LEUCO VAT DYES

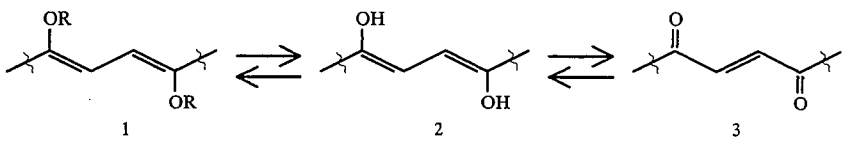

BACKGROUND OF INVENTION

Oxidative dye compositions typically contain a coupler component and a primary intermediate. The coupler component and primary intermediate react in the presence of an oxidant to produce an oxidative dye which has utility in dyeing keratin fibers, such as hair. Typically the process is operated at pH 9–10.

Oxidative hair dyes suffer from certain disadvantages. They do not readily produce the brighter red and yellow colors that are currently fashionable. While such shades may be produced by adding yellow or red nitro dyes, these nitro dyes readily shampoo from hair and the brightness is soon lost, leaving the drabber oxidative color.

A further disadvantage of oxidative hair dyes is that when the process of oxidative hair dyeing is carried out at a low pH, dull drab dyeouts result. In view of the current move towards lower pH and less damaging products, this result is very undesirable.

In view of the above mentioned deficiencies, the value of a method for brightening shades afforded by oxidative dyeing is self-evident.

Solubilized vat dyes are brightly colored pigments, solubilized by reduction to the leuco state. In the leuco form, they are generally only weakly colored. Oxidation regenerates the bright color and insolubilizes the dye, thus making the color very resistant to removal by washing. Solubilized vat dyes are commonly used in the textile art to dye cellulosic fibers.

SUMMARY OF THE INVENTION

In accordance with the present invention, it has been surprisingly found that solubilized vat dyes (or as they are commonly known, "leuco vat dyes") can be oxidized in the relatively mild oxidative systems used in haircoloring to produce strong bright colors. Another surprising feature of the present invention is that the oxidation process of the instant invention is especially effective in mildly acidic solution. Still another surprising feature of the present invention is that the oxidation of the leuco vat dye is sufficiently slow that diffusion of the leuco vat dye into the hair is able to occur before the leuco vat dye oxidizes into an insoluble dye which would otherwise not color hair.

An especially preferred form of the instant invention uses leuco vat esters which readily undergo chemical oxidation to the vat dye or which can reoxidize when subjected to irradiation by light. These leuco vat esters can be depicted by the general formula 1.

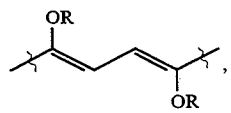

wherein R is preferably $SO_3^-$.

Leuco vat esters in accordance with the above depicted formula 1, undergo hydrolysis and oxidation in accordance with the following reaction scheme:

As depicted above, the leuco vat ester of the formula is hydrolyzed to produce the leuco vat pigment 2 which is oxidized to produce the vat pigment 3.

It should be noted that prior to the instant invention leuco vat pigments had never been employed in oxidative dye systems.

Preferred dyes in accordance with the instant invention include CI Solubilized Vat Brown 5, CI Solubilized Vat Black 1, CI Solubilized Vat Red 1, CI Solubilized Vat Green 2, CI Solubilized Vat Violet 8, CI Solubilized Vat Yellow 4, CI Solubilized Vat Brown 1, and CI Solubilized Vat Red 3.

CI Solubilized Vat Brown 5 corresponds to Color Index Number 73411 and is available from Sandoz as Indigosol Brown IRRD. Its structure is as follows:

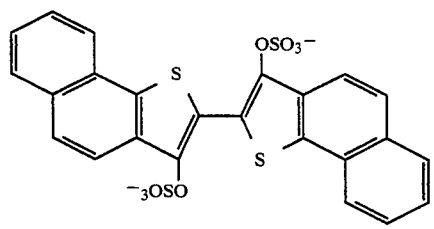

I

CI Solubilized Vat Black 1 corresponds to Color Index 73671. It is available from Sandoz as Indigosol Gray IBL and is also available from Hoechst as Anthrasol Grey IBL. Its structure is depicted as follows:

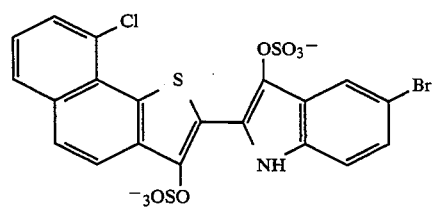

II

CI Solubilized Vat Red 1 corresponds to Color Index 73361. It is available from Sandoz as Indigosol Pink IR and is also available from Hoechst as Anthrasol Pink IR. Its structure is depicted as follows:

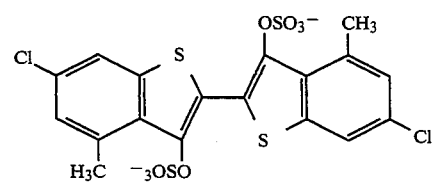

III

CI Solubilized Vat Green 2 corresponds to Color Index 59831. It is the leuco sulfuric acid ester of the dye Indigosol Green IGG which is available from Sandoz and has the following structure.

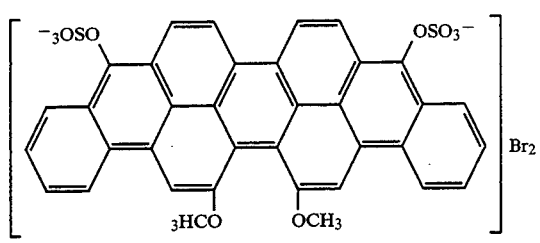

CI Solubilized Vat Violet 8 corresponds to Color Index 73601. It is available from Hoechst as Anthrasol Violet ARR and is also available from Sandoz as Indigosol Violet ARR. Its structure is as follows:

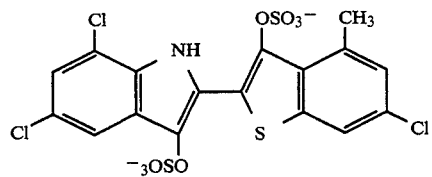

CI Solubilized Vat Red 3 (V) is available from Sandoz. Its structure is not published.

CI Solubilized Vat Yellow 4 corresponds to Color Index 59101. It is the leuco sulfuric acid ester of a dye available from Sandoz as Indigosol Golden Yellow IGK. Indigosol Golden Yellow IGK has the following structure:

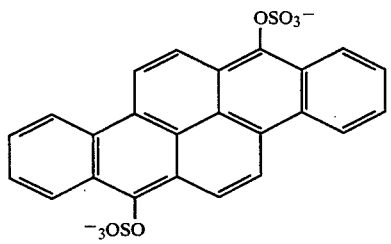

It is also available from Hoechst as Anthrasol Golden Yellow IGK.

CI Solubilized Vat Brown 1 corresponds to Color Index 70801. It is mainly the leuco sulfuric acid ester of a dye available from Hoechst as Anthrasol Brown IBR and available from Sandoz as Indigosol Brown IBR. The structure of the oxidized vat pigment derived from Anthrasol Brown IBR is as follows:

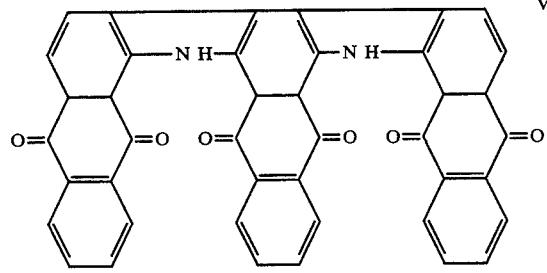

The present invention offers significant advantages to those skilled in the art of oxidative dyeing. Unlike the colors obtained through use of nitro dyes, the colors produced in accordance with the present invention are stable to shampooing and to light. With the present invention, color is produced udder oxidative conditions which allow for the hair bleaching necessary when shades lighter than the original hair color are desired. Advantageously, solubilized vat dyes of the present invention are compatible with current bleaching and oxidative dye color systems. Moreover, although color will form in all pH ranges, color formation in acidic solutions is particular effective. This advantageously allows for brighter shade development with low pH, non-lifting (non-bleaching) permanent dye products, which are currently being marketed.

To demonstrate that the aforementioned advantages are obtained through use of the instant invention, the following examples were carried out. The general procedure utilized was as followed.

GENERAL PROCEDURE

Blended gray hair tresses (1 g) were saturated for 30 minutes with a solution containing dye (10 g/l), 10 g/l of Alcopol O (a surfactant), 300 g/l urea (a penetration enhancer), and 20 g/l sodium metabisulfite. pH was adjusted to 3.5 with acetic acid. The tresses were rinsed and then treated with 12.5 ml of oxidant solution for 20 minutes. The oxidants employed were 40 g/l ammonium persulfate at pH 3 or a 6% hydrogen peroxide solution adjusted to pH 9.5 with ammonia (CLAIROL BORN BLONDE Lightener, prepared according to label instructions). After oxidation, the tresses were rinsed and dried. Before and after dyeing, measurements were taken on a Macbeth Color Eye System to determine the degree of coloration.

Color difference was expressed using L*, a*, and b* values where:
  L* being a measure of lightness given the values 100 for true white and 0 for true black.
  a* being a measure of the greenness or redness. Red being positive and green being negative;
  b* being a measure of the yellowness or blueness. Yellow being positive and blue being negative.

Difference values were calculated as follows:
  $\Delta L^* = L^*sample - L^*standard$
  $\Delta a^* = a^*sample - a^*standard$
  $\Delta b^* = b^*sample - b^*standard$ Generally, deposition of dye results in a decrease in L*, so that $\Delta L^*$ is negative. A more negative number reflects greater dye deposition. Changes in a* and b* are more difficult to interpret since addition of dye can result in changes which are positive or negative depending on the original hair color and the color of the dye. When the leuco dye has a color that is different from that of the vat dye, the change in a* and b* values is influenced.

Using the general procedure outlined above various vat dyes were evaluated. The vat dyes tested were designated as vat dyes I through VIII. These designations correspond to like Roman Numerical designations assigned to the structural formulas for the vat dyes utilizable in the instant invention disclosed earlier in this application.

Color measurement values for dyed tresses oxidized with ammonium persulfate solution at pH 3 are reported in Table I below.

TABLE I

| | DYE | ΔL* | Δa* | Δb* |
|---|---|---|---|---|
| I | Indigosol Brown IRRD | −3.59 | 2.30 | 0.12 |
| II | Anthrasol Grey IBL | −9.16 | −2.99 | −9.30 |
| III | Anthrasol Pink IR | −3.98 | 8.36 | −3.35 |
| IV | Anthrasol Green IGG | −4.27 | −11.01 | −5.50 |
| V | Indigosol Red AB | −4.76 | 4.98 | −4.77 |
| VI | Anthrasol Violet ARR | −3.26 | 3.14 | −7.31 |
| VII | Indigosol Yellow IGK | −1.23 | 4.21 | 12.23 |
| VIII | Anthrasol Brown IBR | −0.56 | 1.68 | −0.12 |

Color measurement values for dyed tresses oxidized with pH 9.5 6% hydrogen peroxide (CLAIROL BORN BLONDE) are reported in Table II below.

TABLE II

| | DYE | ΔL* | Δa* | Δb* |
|---|---|---|---|---|
| I | Indigosol Brown IRRD | −5.54 | 3.33 | 2.99 |
| II | Anthrasol Grey IBL | −5.29 | −1.83 | −0.47 |
| III | Anthrasol Pink IR | −2.39 | 7.98 | −1.69 |
| IV | Anthrasol Green IGG | −7.69 | −17.08 | −5.56 |
| V | Indigosol Red AB | −1.48 | 0.88 | −1.40 |
| VI | Anthrasol Violet ARR | −5.02 | 2.43 | −4.00 |
| VII | Indigosol Yellow IGK | −7.02 | 3.49 | 14.73 |
| VIII | Anthrasol Brown IBR | −5.89 | 1.64 | 0.78 |

The data reported in Tables I and II show color developments for each of the vat dyes listed. While the degree of color developments depends to some extent on the particular vat dye employed, it is clear that a significant color change is produced by the process of the instant invention, both in acid and in alkaline oxidative conditions.

Dyed tresses were subjected to shampooing and exposure to light. All dyed tresses were found to be stable to such shampooing and light exposure.

To demonstrate that the degree of photolytic color formation afforded by the process of the instant invention is reasonably comparably to that produced by chemical processes, the following tests were carried out.

Wool serge was used in the tests rather than hair because the wool substrate can be held flat. Additionally, it is easier to demonstrate and quantitate photolytic dye development on wool serge than on hair.

2 g samples of wool serge were immersed for 30 minutes in a dye bath containing 10 g/l dye, 10 g/l Alcopol O, 300 g/l urea, and 20 g/l sodium metabisulfite. The samples were than rinsed and exposed for 15 minutes on each side to a Microscal tester containing a mercury-tungsten lamp. Color differences were measured as previous described.

Table III below compares the following oxidative treatments with the photolytic color formation:
(b) dyed and oxidized with ammonium persulfate (40 g/l) at pH 3 for 40 minutes;
(c) dyed and oxidized with ammonium persulfate (40 g/l) and hydrogen peroxide (6%) at pH 3 for 40 minutes; and
(a) dyed and subjected to light treatment.

TABLE III

Comparison of the different methods of vat pigment formation.

| | DYE | TREATMENT | ΔL* | Δa* | Δb* |
|---|---|---|---|---|---|
| I | Indigosol Brown | b | −28.51 | 11.81 | 4.52 |
| | | c | −30.64 | 13.37 | 5.68 |
| | | a | −29.16 | 11.24 | 4.95 |
| II | Anthrasol Grey IBL | b | −45.88 | −0.80 | −20.87 |
| | | c | −47.16 | −0.97 | −20.98 |
| | | a | −36.73 | −5.17 | −16.86 |
| III | Anthrasol Pink IR | b | −26.06 | 36.89 | −1.70 |
| | | c | −25.28 | 37.39 | −1.66 |
| | | a | −29.64 | 44.77 | 5.04 |
| IV | Anthrasol Green IGG | b | −31.06* | −18.20* | −6.66* |
| | | c | −27.99 | −12.72 | −4.91 |
| | | a | −41.54 | −25.07 | −11.56 |
| V | Indigosol Red AB | b | −42.00 | 12.67 | −11.43 |
| | | c | −40.66 | 12.47 | −11.75 |
| | | a | −47.13 | 4.67 | −17.19 |
| VI | Anthrasol Violet ARR | b | −37.89 | 19.00 | −25.24 |
| | | c | −39.57 | 19.00 | −25.54 |
| | | a | −35.25 | 16.62 | −29.29 |
| VII | Indigosol Golden Yellow IGK | b | −20.64 | 24.43 | 52.47 |
| | | c | −21.43 | 24.30 | 52.02 |
| | | a | −14.83 | 6.01 | 64.09 |
| VIII | Anthrasol Brown IBR | b | −33.76 | 11.21 | 2.55 |
| | | c | −33.68 | 11.48 | 1.39 |
| | | a | −28.50 | 3.20 | 7.89 |

*These samples were oxidized for 20 minutes.

It is clear from the results reported in Table III that the degree of photolytic color formation was reasonably comparable to that produced by the chemical processes.

What is claimed is:

1. In a mild oxidative haircoloring system comprising a coupler and a primary intermediate, the improvement which consists essentially of adding to the system a color brightening amount of a solubilized vat dye selected from the group consisting of CI Solubilized Vat Brown 5,

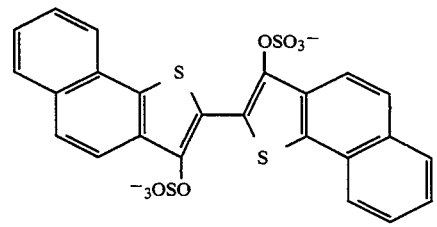

CI Solubilized Vat Black 1,

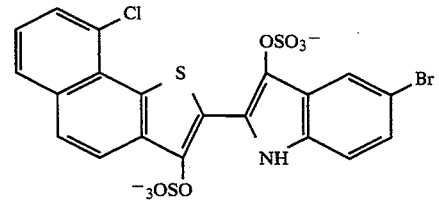

CI Solubilized Vat Red 1,

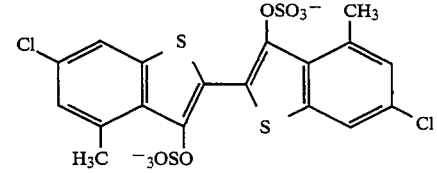

CI Solubilized Vat Green 2,

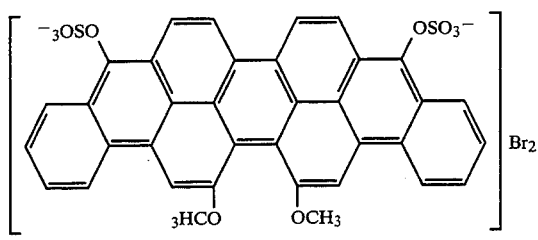

CI Solubilized Vat Violet 8

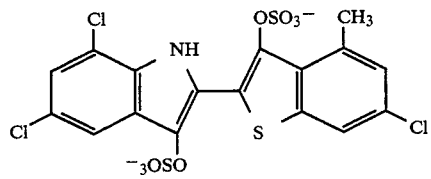

CI Solubilized Vat Yellow 4,

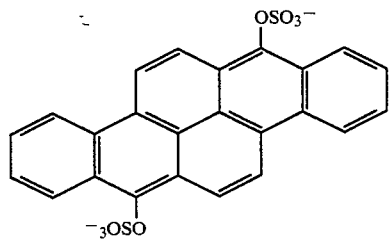

and CI Solubilized Vat Brown 1

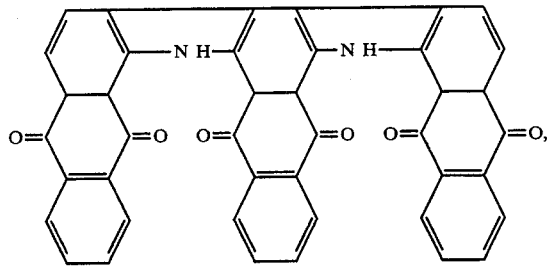

said coupler, primary intermediate, and vat dyes being the sole dyes present in the haircoloring system.

2. The system as claimed in claim 1 wherein the solubilized vat dye is a leuco vat sulfuric ester of the Formula 1,

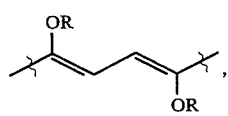

1 wherein R is —SO$_3$Na.

3. In a process wherein hair is colored by contact with a mild oxidative haircoloring system comprising a coupler and a primary intermediate, the improvement consisting essentially of contacting the hair with a color brightening amount of a solubilized vat dye in leuco vat pigment form selected from the group consisting of CI Solubilized Vat Brown 5

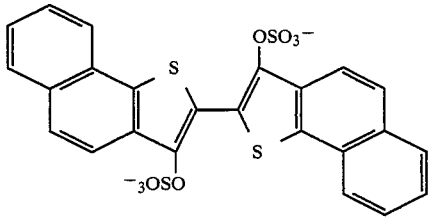

CI Solubilized Vat Black 1,

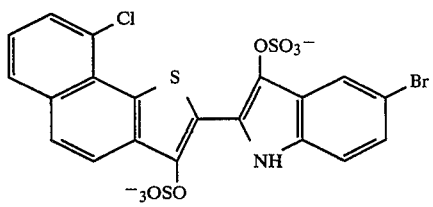

CI Solubilized Vat Red 1,

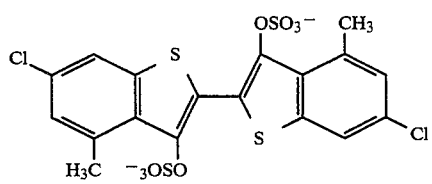

Solubilized Vat Green 2

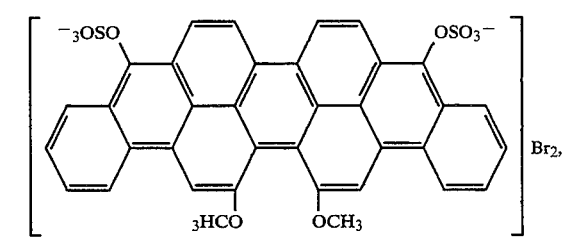

CI Solubilized Vat Violet 8

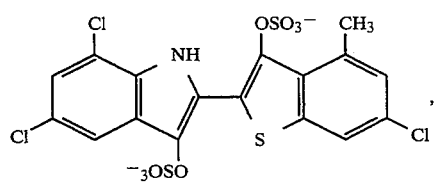

CI Solubilized Vat Yellow 4

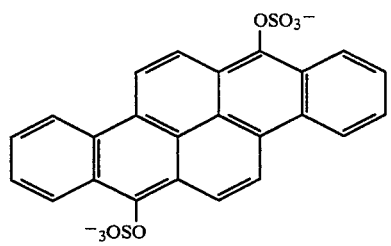

and CI Solubilized Vat Brown 1

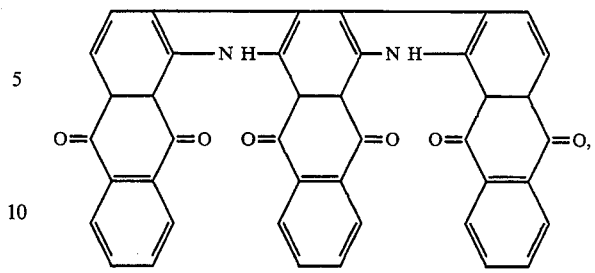

said coupler, primary intermediate, and vat pigments being the sole dyes and pigments present in the haircoloring system.

4. The process as claimed in claim 3, wherein said contacting is carried out at an acidic pH.

5. The process as claimed in claim 4, wherein the pH is about 3.

6. The process as claimed in claim 4, wherein the oxidative system contains ammonium persulfate.

7. The process as claimed in claim 5, wherein the oxidative system contains ammonium persulfate.

8. The process as claimed in claim 3, wherein said contacting is carried out at an alkaline pH.

9. The process as claimed in claim 8, wherein the pH is about 9.5.

10. The process as claimed in claim 8, wherein the oxidative system contains 6% hydrogen peroxide.

11. The process as claimed in claim 10, wherein the hydrogen peroxide is adjusted to pH 9.5 with ammonia.

* * * * *